US009834744B2

(12) United States Patent
Ludwig et al.

(10) Patent No.: US 9,834,744 B2
(45) Date of Patent: Dec. 5, 2017

(54) USE OF AN OXIDISING ALKALINE GEL TO REMOVE A BIOFILM ON A SURFACE OF A SOLID SUBSTRATE

(71) Applicant: COMMISSARIAT A L'ENERGIE ATOMIQUE ET AUX ENERGIES ALTERNATIVES, Paris (FR)

(72) Inventors: Amelie Ludwig, Salon de Provence (FR); Frederic Goettmann, Courthezon (FR); Fabien Frances, Rousson (FR); Romain Castellani, Mougins (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 0 days.

(21) Appl. No.: 15/101,840

(22) PCT Filed: Dec. 3, 2014

(86) PCT No.: PCT/EP2014/076417
§ 371 (c)(1),
(2) Date: Jun. 3, 2016

(87) PCT Pub. No.: WO2015/082548
PCT Pub. Date: Jun. 11, 2015

(65) Prior Publication Data

US 2016/0298060 A1 Oct. 13, 2016

(30) Foreign Application Priority Data

Dec. 5, 2013 (FR) ...................................... 13 62177

(51) Int. Cl.

| | |
|---|---|
| ***A01N 25/04*** | (2006.01) |
| ***A61L 2/18*** | (2006.01) |
| ***C11D 1/66*** | (2006.01) |
| ***C11D 7/06*** | (2006.01) |
| ***C11D 11/00*** | (2006.01) |
| ***C11D 3/04*** | (2006.01) |
| ***C11D 3/12*** | (2006.01) |
| ***C11D 3/37*** | (2006.01) |
| ***C11D 3/39*** | (2006.01) |
| ***C11D 3/395*** | (2006.01) |

(52) U.S. Cl.
CPC .......... *C11D 11/0023* (2013.01); *C11D 3/044* (2013.01); *C11D 3/1213* (2013.01); *C11D 3/3707* (2013.01); *C11D 3/3947* (2013.01); *C11D 3/3956* (2013.01); *C11D 11/0041* (2013.01); *C11D 11/0052* (2013.01)

(58) Field of Classification Search
CPC ........... A01N 25/04; A61L 25/04; C11D 1/66; C11D 3/044; C11D 7/06; C11D 11/0023; C11D 17/043; C11D 17/003
See application file for complete search history.

(56) References Cited

U.S. PATENT DOCUMENTS

| | | | | |
|---|---|---|---|---|
| 4,695,394 A * | 9/1987 | Choy | C11D 3/1213 510/369 |
| 5,089,161 A * | 2/1992 | Ahmed | C11D 17/003 510/221 |
| 6,294,511 B1 * | 9/2001 | Argo | C11D 3/046 510/238 |
| 7,427,170 B2 * | 9/2008 | Van Buskirk | C11D 17/041 252/187.24 |
| 2006/0000495 A1 | 1/2006 | Brown | |
| 2008/0228022 A1 * | 9/2008 | Faure | C11D 3/042 588/18 |
| 2012/0232153 A1 | 9/2012 | Griese et al. | |
| 2013/0023713 A1 | 1/2013 | Labe et al. | |
| 2013/0171024 A1 * | 7/2013 | Cuer | A01N 25/04 422/28 |
| 2015/0307393 A1 | 10/2015 | Guillot et al. | |
| 2016/0016150 A1 | 1/2016 | El Mourabit et al. | |
| 2016/0050911 A1 | 2/2016 | Ludwig et al. | |
| 2016/0057993 A1 | 3/2016 | Ludwig et al. | |

FOREIGN PATENT DOCUMENTS

| | | |
|---|---|---|
| FR | 2 827 530 A1 | 1/2003 |
| FR | 2 891 470 A1 | 4/2007 |
| FR | 2 962 046 A1 | 1/2012 |
| FR | 2 984 170 A1 | 6/2013 |
| WO | 2012/001046 A1 | 1/2012 |
| WO | 2014/154818 A1 | 10/2014 |

OTHER PUBLICATIONS

International Search Report dated Mar. 20, 2015, in PCT/EP2014/076417 Filed Dec. 3, 2014.
French Search Report dated Sep. 9, 2014, in FR 13 62177 Filed Dec. 5, 2013.

(Continued)

*Primary Examiner* — Charles Boyer
(74) *Attorney, Agent, or Firm* — Oblon, McClelland, Maier & Neustadt, L.L.P.

(57) ABSTRACT

The use of a gel consisting of a colloidal solution comprising, preferably consisting of: 5% to 30% by weight, preferably 5% to 25% by weight, more preferably 8% to 20% by weight relative to the weight of the gel, of at least one inorganic viscosifying agent; a mineral base selected from among hydroxides of alkaline metals, hydroxides of alkaline-earth metals and the mixtures thereof, said mineral base being present in a proportion of 0.05 to 10 mol/L of gel, preferably in a proportion of 0.1 to 5 mol/L of gel; an oxidizing agent stable in a basic medium selected from among permanganates, persulfates, ozone, hypochlorites and the mixtures thereof, said oxidizing agent stable in a basic medium being present in a proportion of 0.05 to 5 mol/L of gel, preferably 0.1 to 2 mol/L of gel; 0.1% to 2% by weight relative to the weight of the gel, of at least one surfactant; and a solvent; the gel not containing any superabsorbent polymer, to remove a biofilm present on a surface of a solid substrate.

21 Claims, 4 Drawing Sheets

(56) References Cited

OTHER PUBLICATIONS

Nobatek Report, "Caracterisation des microorganismes se developpant sur les facades en pierre exposees aux embruns marins", http://www.nobatek.c.om/downloads/Etudes%20publiques/ENSEL%20Micro%20biologie%20_NOBATEK_.pdf, 2008,(43 pages).

Briandet, et al., "Biofilms, quand les microbes s'organisent," Quae, 2012 (abstract, 2 pages).

Ammerman, "Algae, the growing problem," interface, Jan. 2007 (6 pages).

* cited by examiner

USE OF AN OXIDISING ALKALINE GEL TO REMOVE A BIOFILM ON A SURFACE OF A SOLID SUBSTRATE

TECHNICAL FIELD

The object of the present invention is the use of an oxidising alkaline gel to remove a biofilm from a surface of a solid substrate.

The technical field of the invention can be defined as the treatment of surfaces polluted, soiled, deteriorated by biofilms for the purpose of removing these biofilms from these surfaces and of improving especially the visual appearance of these surfaces.

The invention can be applied to all kinds of surfaces such as organic polymer surfaces e.g. in plastic materials glass material surfaces; cement material surfaces such as cements, slurries, mortars and concrete; baked or unbaked clay surfaces; brick or roof tile surfaces; plaster surfaces; ceramic surfaces; surfaces in natural or artificial stone; rendered surfaces; fibreglass surfaces; fibrocement surfaces; asphalt or tar surfaces; metal or metal alloy surfaces e.g. steel or galvanised steel or zinc; and surfaces in cellulose-based materials such as wood. These surfaces may or may not be painted.

The invention particularly applies to the removal of biofilms on outdoor surfaces, in open air, of buildings, constructions and works of art or engineering structures.

However the invention can also be applied to biofilms on surfaces of aquatic craft e.g. sailing vessels; land vehicles such as cars, trucks or motorcycles; aircraft such as fixed wing aircraft, helicopters, hydroplanes or drones; various domestic appliances and equipment such as furniture; industrial apparatus and devices such as piping, in particular apparatus and devices contained in very humid environments or in which cold spots occur; and agri-food products in particular compact agri-food products; or medical devices and apparatus.

It is to be noted that there are no limitations as to the surface from which biofilms are to be removed according to the invention. Whilst in temperate climates the surfaces on which biofilms may develop are rather limited, this is not the case in humid tropical climates where biofilms are likely to affect almost all surfaces.

STATE OF THE PRIOR ART

Outdoor building materials i.e. in open air such as stones, bricks, rendering, roof tiles are continually exposed to various atmospheric agents likely to cause deterioration thereof such as wind, rain, sun or humidity.

In addition to the action of these atmospheric agents is to be considered the effect of biological agents such as microorganisms capable of developing on any surface in the form of biofilms.

With the industrial era, the concentration of organic and inorganic compounds in the air has vastly increased aggravating the process of formation of these biofilms which have the double disadvantage of being displeasing to the eye since they are mostly black, red or green in colour and of leading to accelerated deterioration of building materials known as biodeterioration.

The term biofilm is routinely used in this technical field and has a widely recognised and accepted meaning.

Biofilms can be defined as own ecosystems essentially formed of associations of algae, fungi, bacteria and cyanobacteria, bathing in a gel or matrix of exopolymers protecting them against outside attack and making them highly resistant (see document [1]).

The removal of biofilms is therefore much more difficult than the removal or mere microorganisms since in biofilms the microorganisms are structurally surrounded, protected by exopolymers.

A definition of biofilms is also given in document US-A1-2012/0232153 [2] paragraph [0019], to which reference can be made.

The interior of buildings is not devoid of problems related to the development of biofilms. Wet areas in particular bathrooms, wash rooms, cold spots in bedrooms are sites of choice for the onset of black stains i.e. biofilms (see « *Biofilm quand les microbes s'organisent* » by R. Briandet, L. Fechner, M. Naïali and C. Dreano, Editions Quae 2012 [3]). Again, in addition to an obvious unsightly problem these biofilms can give rise to problems of human health related to allergies they may cause in some persons.

To remove these biofilms and the stains related to the formation thereof numerous cleaning and washing techniques are currently used.

Table 1 below gives a non-exhaustive list of these techniques with their main advantages and disadvantages.

TABLE 1

List of cleaning techniques most frequently used to remove stains related to biofilm formation.

| Cleaning technique | Application | Advantages | Disadvantages | Reference |
|---|---|---|---|---|
| High pressure jet | Outdoor | High efficiency<br>Possible to treat large surface areas<br>Non-polluting. | Risk of material degradation (abrasion)<br>Risks of spraying and soiling other parts of the building<br>No protective effect. | K. Ammerman, « *Algae, the growing problem* », Interface, January 2007, pages 37 to 42 [4]. |
| Steam cleaning | Indoor | Non-polluting. | Difficult to remove all staining<br>Risks of damage to coatings | |
| Washing with surfactant solutions | Indoor/ Outdoor | Non-polluting (generally)<br>Ease of use. | Limited efficiency. | |

TABLE 1-continued

List of cleaning techniques most frequently used to remove stains related to biofilm formation.

| Cleaning technique | Application | Advantages | Disadvantages | Reference |
|---|---|---|---|---|
| Washing with bleach solutions | Indoor/ Outdoor | High efficiency Combines disinfecting action with bleaching. | Compound toxic for plants Risk of chemical burns Rinsing effluent discharged into rainwater circuits. | K. Ammerman, « *Algae, the growing problem* », Interface, January 2007, pages 37 to 42 [4]. |
| Washing with peroxide solutions (e.g. hydrogen peroxide) | Indoor/ Outdoor | High efficiency Combines disinfecting action with bleaching No residual toxicity. | Risk of chemical burns Rinsing effluent discharged into rainwater circuits. | K. Ammerman, « *Algae, the growing problem* », Interface, January 2007, pages 37 to 42 [4]. |
| Washing with base solutions | Indoor/ Outdoor | Average efficiency (no bleaching action). | Compound toxic for plants (at high dose) Risk of chemical burns Rinsing effluent discharged into rain water circuits. | K. Ammerman, « *Algae, the growing problem* », Interface, January 2007, pages 37 to 42 [4]. |
| Washing with hydroalcoholic solutions | Indoor/ Outdoor | High efficiency Combines disinfecting and detergent action. | Potential high cost Rinsing effluent discharged into rain water circuits. | G.G. Griese et al. « *Acidic biofilm remediation* » US - A1-2012/0232153 [2] |
| Formulated gels (Fungicides + polymers) | Outdoor | High efficiency Provide longer-term protection | Potentially high cost Leaching of fungicide into rainwaters. | K. Ammerman, « *Algae, the growing problem* », Interface, January 2007, pages 37 to 42 [4]. |

As can be seen in Table 1, most techniques available exhibit sufficient efficacy. On the other hand, all have a certain number of disadvantages essentially due to the fact that they carry risks for the surface to be treated and/or for the operator and/or for the environment.

In addition, in the field of nuclear decontamination, gelled formulations which overcome problems related to the powdery nature of the dry waste and increase the efficacy of the method by using a gel, were the subject of documents [5] and [6].

These documents describe inorganic colloid gels known as « suctionable gels », specifically formulated to be sprayed and to fracture on drying whilst trapping and confining radioactive contamination in the form of suctionable, non-powdery flakes that can be directly packaged and stored.

Document [5] describes a gel formed of a colloidal solution comprising an inorganic viscosifying agent, generally silica or aluminium oxide, an active treatment agent e.g. an inorganic acid or base such as sodium hydroxide or potassium hydroxide and optionally an oxidising agent having a standard redox potential $E_0$ higher than 1.4 V in a strong acid medium such as Ce(IV), Co(III) or Ag(II).

Document [6] describes a gel formed of a colloidal solution comprising an inorganic viscosifying agent, generally silica or aluminium oxide, a surfactant, an inorganic acid or base, optionally an oxidising agent having standard redox potential $E_0$ higher than 1.4 V in a strong acid medium such as Ce(IV), Co(III) or Ag(II).

The rheology of these inorganic colloidal gels, on account of the different constituents of their composition, allows spraying thereof onto a contaminated surface followed by their adhesion to this surface, even a vertical surface, without run-off.

This therefore provides extended contact between the contaminant and the active decontamination agent, without any damage to the mechanical properties of the substrate.

After spraying the gel dries, breaks up and produces dry residues called « flakes » adhering to the substrate which can subsequently be removed by brushing or suction and directly packaged.

Decontamination methods using these suctionable gels are therefore dry decontamination methods not generating any liquid effluent and very few dry solid residues. These dry solid residues on average only represent one quarter of the mass of the initially sprayed gel. In addition, these methods limit operator exposure time to radioactive contamination since they are easy to apply by spraying followed by suctioning of the dry residues, and also because the presence of the operator is not required during the gel drying time.

However, the gels described in documents [5] and [6] are specifically intended for radioactive decontamination of surfaces, in particular when dismantling nuclear plants, and are not in any manner adapted for the removal of surface biofilms or even able to be adapted to solve the extremely specific problem of removing biofilms from surfaces.

Documents FR-A1-2962046 and WO-A1-2012/001046 [7] concern a « suctionable » biological decontamination gel and a biological decontamination method to decontaminate surfaces using this gel.

This gel is formed of a colloidal solution comprising at least one inorganic viscosifying agent, at least one biological decontamination agent, at least one super-absorbent polymer and at least one surfactant.

The super-absorbent polymer such as sodium polyacrylate allows improved efficacy of the gel on porous materials e.g. mortars.

However the gel in document [7] is specifically intended for the biological decontamination of surfaces and in particular for so-called post-event clean-up of surfaces.

There is no mention or suggestion in document [7] that the gel in this document is able to allow the solving of the very specific problem of removing biofilms from surfaces, which is a problem fully differing from the problem of biological decontamination—post-event decontamination in particular—due to the very particular and highly complex nature of biofilms.

The biological decontamination of a surface simply entails removing biological species that are essentially biotoxic, isolated, dispersed and exposed without any protection on this surface, whereas biofilms are complex systems in which populations of microorganisms are surrounded and protected by polysaccharides and other macromolecules commonly called exopolysaccharides. The problems raised by the removal of biofilms are therefore fully different and certainly more complex and more difficult than those encountered when decontaminating a surface contaminated only with isolated biological species. The fact that a gel has been successfully used for the biological decontamination of a surface in no way means that this same gel could be suitable for removing biofilms in which the microorganisms are protected by an exopolysaccharide gel which must first be destroyed. In addition, a biofilm further comprises numerous other components contributing in particular to its unpleasing colour e.g. red or black which must also be removed to restore the original appearance of the surface, free of soiling.

It has also been evidenced that the gel in document [7] has a very short preservation time e.g. a few weeks.

In the light of the foregoing, there is therefore a need for a technique to remove biofilms from the surface of substrates which, whilst having high efficacy at least as high as with the techniques listed in Table 1, does not have the disadvantages, defects and shortcomings of these techniques.

It is the goal of the present invention inter alia to meet this need.

DESCRIPTION OF THE INVENTION

It has surprisingly been evidenced according to the invention that the use of a gel having a specific composition allowed the aforementioned goal to be reached and to obtain removal of biofilms.

The object of the invention is therefore the use of a gel consisting of a colloidal solution comprising, preferably consisting of:

- 5% to 30% by weight, preferably 5% to 25% by weight, further preferably 8% to 20% by weight relative to the weight of the gel, of at least one inorganic viscosifying agent;
- a mineral base selected from among hydroxides of alkaline metals, hydroxides of alkaline-earth metals and mixtures thereof, said mineral base being present in a proportion of 0.05 to 10 mol/L of gel, preferably in a proportion of 0.1 to 5 mol/L of gel;
- an oxidising agent stable in a basic medium selected from among permanganates, persulfates, ozone, hypochlorites and mixtures thereof, said oxidising agent stable in a basic medium being present in a proportion of 0.05 to 5 mol/L of gel, preferably 0.1 to 2 mol/L of gel;
- 0.1% to 2% by weight relative to the weight of the gel, of at least one surfactant;
- and a solvent;

the gel not containing any super-absorbent polymer, to remove a biofilm present on a surface of a solid substrate.

It can generally be considered that the colloidal solution comprises «the remainder (balance) solvent».

By «the remainder (balance)» is meant that the solvent is always contained in the colloidal solution and that the amount of solvent is such that when added to the amounts of components of the colloidal solution other than the solvent (whether these components are compulsory or optional components cited above, or other cited or non-cited optional additional components), the total amount of all the components of the colloidal solution is 100% by weight.

The use of the above-described specific gel to remove a biofilm present on a surface of solid substrate has never been described in the prior art.

The gel used in the invention according to a first fundamental characteristic is first defined by the fact that it contains the combination of a specific mineral base selected from among hydroxides of alkaline metals, hydroxides of alkaline-earth metals and the mixtures thereof, and of a specific biocide oxidising agent which is an oxidising agent stable in a basic medium selected from among permanganates, persulfates, ozone, hypochlorites and the mixtures thereof, and a surfactant.

The gel used in the invention is a basic gel i.e. having a pH generally higher than 7, preferably of 12 to 14, and by basic medium is meant a medium having a pH generally higher than 7, preferably 12 to 14.

The gel used in the invention is then defined by the fact that it does not contain any super-absorbent polymer.

It can be said that the association of a specific mineral base such as an alkaline hydroxide e.g. sodium hydroxide or a hydroxide of an alkaline-earth metal, of a specific oxidising agent such as a hypochlorite e.g. sodium hypochlorite having biocidal action, and finally of a surfactant forms a true synergic combination as is explained below.

The gel used in the invention has high efficiency for the removal of biofilms due to the combination of the decontaminating, biocidal and bleaching action of the oxidising agent such as bleach ("Javel"), and of the degreasing action of the mineral base such as sodium hydroxide and of the surfactant.

It is this combination of the effects due to the oxidising agent, to the base and to the surfactant which makes the gel extremely efficient when removing biofilms.

In addition, the specific oxidising agent such as bleach ("Javel") is not just an oxidising species it is also an excellent biocide, in other words aside from its degreasing action the mineral base such as sodium hydroxide therefore also has biocidal action.

The gel used in the invention which contains the combination of a specific mineral base such as an alkaline metal hydroxide e.g. sodium hydroxide or an alkaline-earth metal hydroxide, and of specific oxidising agent such as a hypochlorite e.g. sodium hypochlorite has reinforced biocidal action in particular compared with gels such as those in document [7] only containing a mineral base such as sodium hydroxide.

It can be estimated that the use according to the invention indeed comprises two biocidal compounds namely a first active biocidal compound which is a mineral base such as sodium hydroxide and a second active biocidal compound which is an oxidising agent such as bleach.

It is the combination of these two compounds which makes the gel even more efficient against biological species of the biofilm, whilst the degreasing, oxidising and bleaching properties which the gel also has ensure total removal, destruction of all the components of the biofilm. In particular the unpleasing «dirty» colour imparted to the surface by the biofilm is removed by the gel used according to the invention, and the treated surface is restored to its original, initial, «clean» colour that it initially had before formation of the biofilm.

Even more surprisingly the gel used in the invention, which is therefore highly efficient in removing biofilms, is nevertheless stable and shows increased stability over time.

The inventors have effectively evidenced that the poor stability over time of the biological decontamination gel in document [7] is due to the super-absorbent polymer since this super-absorbent polymer modifies the rheology of the gel during storage thereof making it unsuitable for spraying and application to a vertical surface on account of poor adhesion.

The inventors have additionally evidenced that the use of oxidising agents in the presence of super-absorbent polymers causes further considerable reduction in the the stability over time of the biological decontamination gel [7], down to a time of less than a few days.

The absence of any super-absorbent polymer in the gel used in the invention therefore largely improves the stability thereof over time.

It is fully unexpected and surprising that according to the invention the above-described gel could be used to remove a biofilm from solid surfaces and ensure highly efficient removal of these biofilms attributable to the synergic combination of the actions and effects of each of its constituents. According to the invention, after use of the gel, a cleaned surface is obtained that is rid of the biofilm, without any soiling and unpleasing staining, having an appearance close to its initial, original, appearance before formation of the biofilm.

The efficiency of the use according to the invention is demonstrated in Examples 2, 3 and in the Figures illustrating these examples.

Preferably the mineral base is selected from among sodium hydroxide, potassium hydroxide and the mixtures thereof, and the oxidising agent stable in a basic medium is selected from among hypochlorites and the mixtures thereof.

One particularly preferred gel contains a combination of sodium hydroxide and sodium hypochlorite.

In this case, the sodium hydroxide is contained in a proportion of 0.05 to 10 mol/L gel, preferably 0.5 to 5 mol/L gel, and the sodium hypochlorite is contained in a proportion of 0.05 to 5 mol/L gel, preferably 0.1 to 1.5 mol/L gel.

The addition of sodium hypochlorite (concentrated bleach) allows reinforced biocidal aggressiveness of the gel used compared with a gel only containing sodium hydroxide, without fundamentally modifying its physicochemical properties or rheology.

Sodium hydroxide is also a good biocide. In addition, it is an excellent stabiliser of sodium hypochlorite and guarantees good preservation of the hypochlorite ion content whilst ensuring a biocidal function.

To summarise, the use according to the invention allows all the above-mentioned needs to be met.

The use according to the invention provides a solution to the problems raised by known biofilm removal techniques such as those listed in Table 1, without having the disadvantages thereof.

In particular, the use according to the invention does not carry any risk for the support, substrate to be treated and/or for the operator and/or for the environment.

The gel used in the invention is a colloidal solution which means that the gel used according to the invention contains inorganic, mineral solid particles of a viscosifying agent of which the size of the elementary, primary particles is generally 2 to 200 nm.

On account of the use of a viscosifying agent generally exclusively inorganic without any organic viscosifying agent, the content of organic matter in the gel used according to the invention is generally lower than 4% by weight, preferably lower than 2% by weight which amounts to a further advantage of the gels used according to the invention.

These inorganic, mineral, solid particles act as viscosifying agent to allow the solution e.g. the aqueous solution to gel and thereby adhere to the surfaces to be treated, irrespective of their geometry, their shape, their size and irrespective of the location of the biofilms to be removed.

Advantageously the inorganic viscosifying agent can be selected from among metal oxides such as aluminas, metalloid oxides with the exception of silica, metal hydroxides, metalloid hydroxides, metal oxyhydroxides, metalloid oxyhydroxides, aluminosilicates, clays such as smectite, and the mixtures thereof; these viscosifying agents are stable in a basic medium.

In particular, the inorganic viscosifying agent can be selected from among aluminas ($Al_2O_3$).

The inorganic viscosifying agent may only comprise a single aluminium oxide or mixture thereof, namely a mixture of two or more different aluminas ($Al_2O_3$/$Al_2O_3$ mixture).

The alumina can be selected from among calcined aluminas, ground calcined aluminas and the mixtures thereof.

As an example mention can made of the product sold by EVONIK INDUSTRIES under the trade name «Aeroxide Alu C» which is fine-particle, fumed aluminas with a BET specific surface area of 100 $m^2/g$.

Advantageously according the invention, the inorganic viscosifying agent consists of one or more aluminas. This or these aluminas generally represent 5 to 30% by weight relative to the weight of the gel.

In this case, the alumina(s) are preferably at a concentration of 8% to 17% by weight relative to the total weight of the gel (to ensure drying of the gel at a temperature between 20° C. and 50° C. and at relative humidity of between 20% and 60% on average in 30 minutes to 5 hours).

The type of mineral viscosifying agent, in particular when consisting of one or more aluminas, influences in an unexpected way the drying of the gel used according to the invention and the particle size of the residue obtained.

The dry gel is in the form of particles of controlled size, more specifically solid flakes of millimeter size generally ranging from 1 to 10 mm, preferably 2 to 5 mm due in particular to the aforementioned compositions, particularly when the viscosifying agent consists of one or more aluminas.

It is specified that the particle size generally corresponds to their largest dimension.

The gel used according to the invention contains a specific mineral base and a specific oxidising active agent such as defined above.

This specific base and specific oxidising agent can particularly be termed biocidal agents.

By biocidal agent is meant that when it is contacted with a biological species contained in a biofilm it can inactivate or kill this species.

By biological species is meant any type of microorganism which can be found in a biofilm such as bacteria, fungi, yeasts, viruses, toxins, spores and protozoa.

The base and oxidising agent are used at the concentrations mentioned above, to guarantee a biofilm removal capability compatible with the gel drying time, and for example to ensure drying of the gel at a temperature between 20° C. and 50° C. and under relative humidity of between 20% and 60% on average in 30 minutes to 5 hours.

It is again to be noted that the gel used in the invention, being a basic gel, in addition to its biocidal and bleaching action also has degreasing action. The surfactant also contributes towards this degreasing action.

To reach full efficiency including under the most unfavourable climate conditions with regard to gel drying time, the gel used according to the invention may have a wide range of mineral base(s) concentrations.

An increase in concentration of mineral base such as NaOH or KOH, acting in particular as biocidal agent, allows a considerable increase in biofilm removal rate.

The mineral base is used at the above-defined concentration to ensure drying of the gel at a temperature between 20° C. and 50° C. and under relative humidity of between 20% and 60% on average in 30 minutes to 5 hours.

When treating a cement matrix, the basic pH of the gel induced for example through the use of sodium hydroxide or potassium hydroxide allows the prevention of acid-base reactions between the material to be decontaminated and the gel, which could harm the integrity of the material but also the integrity of the gel on the surface and hence the efficiency of the method.

The hygroscopic nature of sodium hydroxide or potassium hydroxide also amounts to a considerable advantage for slowing of the gel drying phenomenon. The contact time between the gel and the biofilm is thereby considerably increased.

The competition between the evaporation process of the aqueous phase and that of water uptake by the crystals of sodium hydroxide or potassium hydroxide favourably modifies the kinetics of gel drying.

The gel used according to the invention, contrary to the gel described in document [7], does not contain any super-absorbent polymer, in other words the gel used in the invention is free of super-absorbent polymer.

By « super-absorbent polymer» also called « SAP» is generally meant a polymer that is capable in the dry state of spontaneously absorbing at least 10 times, preferably at least 20 times its weight of aqueous liquid, water in particular and particularly distilled water. Such super-absorbent polymers are described in detail in aforementioned document [7].

The gel used according to the invention contains a surfactant or mixture of surfactants, preferably selected from among non-ionic surfactants such as block, sequenced, copolymers such as block copolymers of ethylene oxide and propylene oxide, and ethoxylated fatty acids; and the mixtures thereof.

For this type of gel, the surfactants are preferably block copolymers marketed by BASF under the trade name "Pluronic®". For example use can be made of Pluronic® PE6200.

Pluronics® are block copolymers of ethylene oxide and propylene oxide.

As indicated above, just like the base, the surfactant(s) have degreasing action which contributes towards removal of the biofilm.

These surfactants also influence the rheological properties of the gel, in particular the thixotropic nature of the product and the recovery time in order to make it sprayable onto floors, walls or ceilings with no run-off.

The surfactants also provide control over adhesion of the dry waste and over the flake size of the dry residue to guarantee that the waste is non-powdery. Finally these surfactants provide control over the phenomenon of gel bleeding over time and thereby improve its spraying capability after storage.

The solvent of the invention is generally selected from among water, organic solvents and the mixtures thereof.

One preferred solvent is water and in this case the solvent is therefore consisting of water, comprises 100% water.

Advantageously the gel used in the invention may also comprise one or more mineral pigments such as iron oxide.

In general, in the use of the invention at least one cycle is performed comprising the following successive steps:

a) the gel such as described above is applied on said surface;

b) the gel is maintained on the surface at least for a sufficient time so that the gel destroys the biofilm, and so that the gel dries and forms a dry, and solid, non-powdery residue containing compounds resulting from destruction of the biofilm;

c) the dry, solid, non-powdery residue containing the compounds resulting from biofilm destruction is removed.

In general the solid residue does not contain any living biological species and the compounds resulting from biofilm destruction do not contain any living biological species.

The biological species initially contained in the biofilm are killed, destroyed under the action of the gel and the destroyed, « killed», « dead» biological species included in the compounds resulting from destruction of the biofilm are recovered in the dry, solid residue, namely generally in the dried gel flakes.

Advantageously, the substrate is made of at least one material selected from among metals and alloys such as stainless steel, galvanised steel, or zinc; painted steels; organic polymers such as plastic materials or rubbers such as poly(vinyl chloride)s or PVC, polypropylenes or PP, polyethylenes or PE, in particular high density polyethylenes or HDPE, poly(methyl methacrylate)s or PMMA, poly(vinylidene fluoride)s or PVDF, polycarbonates or PC; glasses; cement materials such as pastes, cements, mortars and concretes; plasters; bricks; roof tiles; baked or unbaked earth, clay; natural or artificial stones; coats ("enduits"); glass fibre; fibro-cements; asphalt; tar; slate; cellulose-based materials such as wood; and ceramics.

The substrate may or may not be painted.

Advantageously the gel is applied to the surface of the solid substrate, on which the biofilm has formed, in a proportion of 100 g to 2000 g gel per $m^2$ of surface area, preferably 500 to 1500 g gel per $m^2$ of surface area, more preferably 600 to 1000 g per $m^2$ of surface area, which generally corresponds to a gel thickness deposited on the surface of between 0.5 mm and 2 mm.

Advantageously the gel is applied to the surface of the solid substrate by spraying, or using a brush or float.

Advantageously (at step b)) drying is performed at a temperature of 1° C. to 50° C., preferably 15° C. to 25° C., under relative humidity of 20% to 80%, preferably 20% to 70%.

Advantageously the gel is left on the surface for a time of 2 to 72 hours, preferably 2 to 48 hours, further preferably 3 to 24 hours.

Advantageously the dry, solid residue is in the form of particles e.g. flakes 1 to 10 mm in size, preferably 2 to 5 mm.

Advantageously the dry, solid residue is removed from the surface of the solid substrate by brushing and/or suctioning.

Advantageously the above-described cycle can be repeated 1 to 10 times for example using the same gel for all cycles or using different gels for one or more cycle(s).

Advantageously during step b) the gel, before complete drying is re-wetted with a solution of mineral base and oxidising agent, preferably with the solution of mineral base and oxidising agent applied during step a) in the solvent of this gel.

In other words, during step b) the gel before complete drying can be re-wetted with the solution of mineral base and oxidising agent contained in the gel already described above, which generally avoids having to repeat application of the gel to the surface thereby obtaining savings in reagent and a limited amount of waste. This re-wetting operation can be repeated.

To summarise, the use of the gel of the invention inter alia has the following advantageous properties:

- the gel is an inorganic gel avoiding risks of spattering and surface staining;
- high efficiency related to the combination of the following effects:
  - decontaminating and bleaching action of the oxidizing agent;
  - degreasing action of the base and surfactants;
- very easy application e.g. using a brush, individual spray or paint gun;
- adhesion to walls;
- treatment via dry process of a very broad range of materials;
- no mechanical or physical deterioration of materials after treatment, in particular the gel used is fully innocuous for most building materials on account of its basic character;
- application of the method under variable climate conditions;
- reduction in volume of waste;
- easy recovery of dry waste;
- risks of pollution limited through the formation of flakes which can easily be collected e.g. by suction or brushing and which therefore not enter into rainwater draining networks;
- low operator exposure to the biological species contained in the biofilm and to residues.

Finally, it is noted that the use of the invention, contrary to the techniques set forth above (Table 1), does not carry any risk for the support, substrate to be treated and/or for the operator and/or for the environment.

Other characteristics and advantages of the invention will become better apparent on reading the following detailed description, this description being given as a non-limiting illustration with reference to the appended drawings.

BRIEF DESCRIPTION OF THE DRAWINGS

In FIG. 2B, the distance (in pixels) is plotted along the X-axis and the grey levels along the Y-axis.

DETAILED DESCRIPTION OF PARTICULAR EMBODIMENTS

Figure 1:
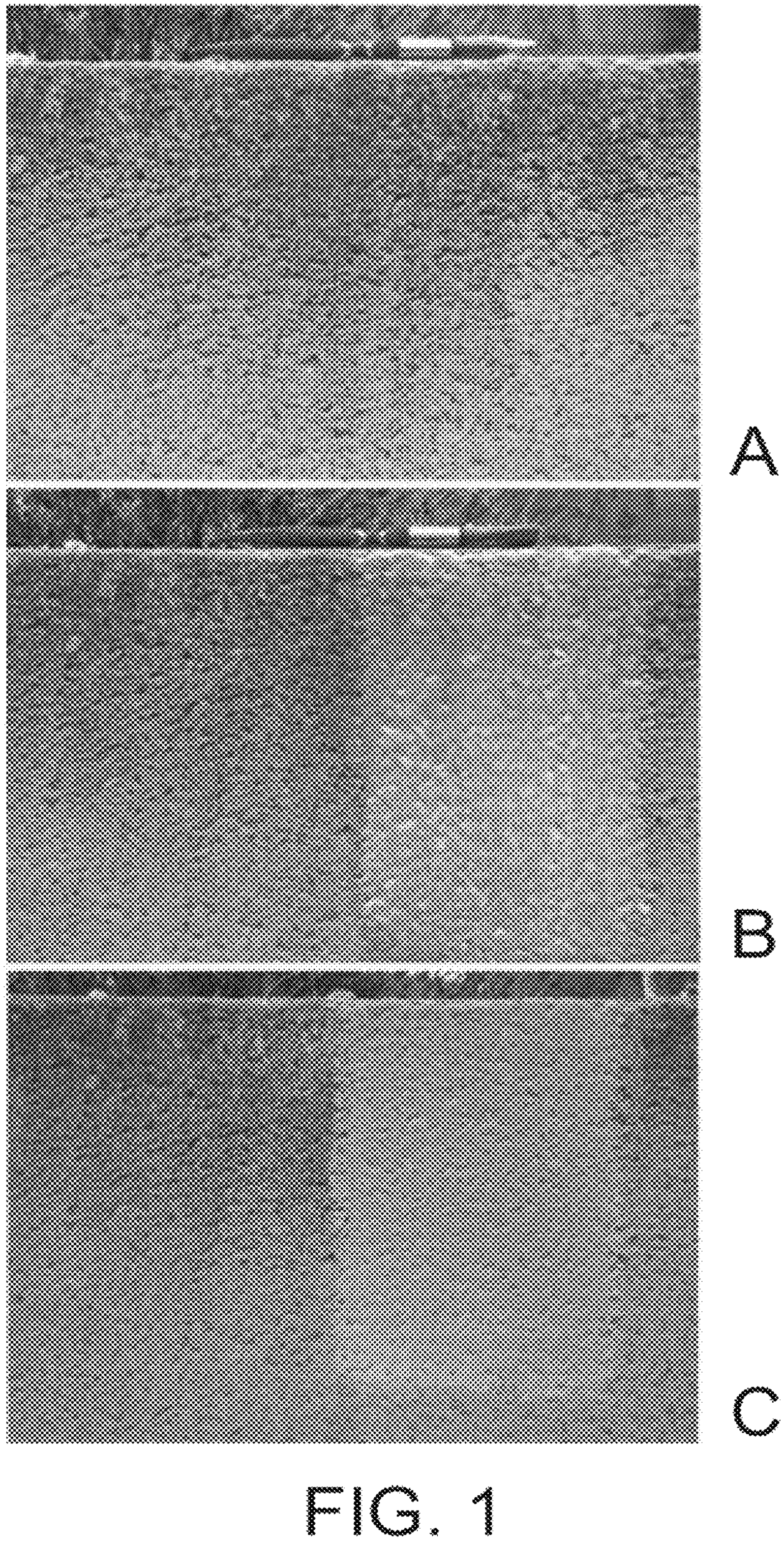
FIG. 1 (A, B, C) gives photographs showing the appearance of the surface of a wall treated according to the invention, at the different steps of the test conducted in Example 2, namely: the initial state of the wall surface (A); the appearance of the wall surface after application of the gel to part of the wall surface using a brush (B); the appearance of the wall surface after 48-hour drying and removal of the dry gel flakes by gentle brushing (C).

The gel used in the invention can easily be prepared at ambient temperature.

For example the gel used in the invention can be prepared by adding, preferably gradually, the inorganic viscosifying agent(s) e.g. the aluminium oxide(s) and/or the silica(s) to a solution containing the combination of an inorganic base and oxidising agent, the surfactant(s) and optional pigment(s). This solution can be prepared for example by first preparing a solution of oxidising agent e.g. a solution of sodium hypochlorite in demineralised water then mixing, together with this solution of oxidising agent, the mineral base, the surfactant(s) and optional pigment(s). This mixing can be performed by mechanical agitation e.g. using a mechanical agitator equipped with a three-blade impeller. The rotation speed is 200 rpm for example and agitation time 3 to 5 minutes for example.

The adding of the inorganic viscosifying agent(s) to the solution containing the mixture of an inorganic base and oxidising agent, the surfactant(s) and optional pigment(s) can be conducted simply by pouring the viscosifying agent(s) into said solution. When adding the inorganic viscosifying agent(s) the solution containing the mixture of an inorganic base and oxidising agent, the surfactant(s) and optional pigment(s) is generally held under mechanical agitation.

For this agitation a mechanical agitator can be used for example equipped with a three-blade impeller.

The agitation speed is generally gradually increased as and when the viscosity of the solution increases, to reach a final agitation speed of between 400 and 600 rpm for example without any spattering.

On completion of the addition of the mineral viscosifying agent(s) agitation is continued for 2 to 5 minutes for example to obtain a fully homogeneous gel.

Other protocols can evidently be followed to prepare the gels used in the invention, with the gel components being added in a different order to the order given above.

In general, the gel used in the invention must have viscosity lower than 200 mPa·s under shear of 1000 $s^{-1}$ to allow spraying onto the surface to be decontaminated either at a distance (e.g. at a distance of 1 to 5 m) or in the vicinity thereof (e.g. at a distance shorter than 1 m, preferably 50 to 80 cm). The setting time of the viscosity must generally be shorter than one second and the viscosity under low shear higher than 10 Pa·s so as not to run off the wall surface.

It is to be noted that the surfactant of the gel used in the invention has a distinct, favourable impact on the rheological properties of the gel used in the invention. This surfactant particularly allows spraying of the gel used in the invention avoiding risks of run-off or dripping when treating vertical surfaces and ceilings. This surfactant also allows limiting of the bleeding phenomenon observed during storage of the gel.

The gel thus prepared is then applied to the solid surface to be cleaned of a substrate made of a solid material.

By solid surface to be cleaned is meant a solid surface on which a biofilm has formed that it is desired to remove.

Possibly aside from alloys of lightweight metals of aluminium type, there is no limitation as to the constituent material of the surface to be cleaned; the gel used allows the treatment of all kinds of materials, even fragile materials, without any damage.

The gel used in the invention does not generate any deterioration, erosion, chemical, mechanical or physical attack of the treated material. The gel used in the invention is therefore not in any way harmful to the integrity of the treated materials and even allows reuse thereof. Therefore sensitive materials such as military equipment are preserved and can be reused after cleaning, whilst monuments, buildings, works of art such as sculptures treated with the gel of the invention are absolutely not degraded and have their visual and structural integrity preserved.

This substrate material can therefore be selected from among metals or alloys for example such as stainless steel, polymers such as plastic materials or rubbers of which mention can be made of PVCs, PPs, PEs in particular HDPEs, PMMAs, PVDFs, PCs, glasses, cements, mortars and concretes; plasters, bricks, natural or artificial stone, coats, ceramics.

In all cases (see Examples 2 and 3 and Figures), irrespective of material type e.g. coat or cement, the cleaning of the invention has total efficiency.

The treated surface may or may not be painted.

There is therefore no limitation with regard to shape, geometry and size of the surface to be cleaned; the gel used according to the invention allows the treatment of surfaces of large size, of complex geometries having hollows, corners, recesses for example.

The gel used in the invention ensures the efficient treatment not only of horizontal surfaces such as floors or balcony rails or window sills, but also of vertical surfaces such as walls, facades or inclined or overhanging surfaces such as ceilings.

Compared with existing techniques which use liquids such as solutions, the invention uses a gel which is particularly advantageous for the treatment of materials having a large surface area that cannot be transported and are located outdoors. The method of the invention, through use of a gel, allows in situ cleaning preventing the spill of chemical solutions into the environment and the dispersion of contaminating species.

The gel of the invention can be applied to the surface to be treated using any application method known to the man skilled in the art.

Conventional methods are spraying for example using a spray gun or application using a brush or float.

For application by spraying of the gel onto the surface to be treated, the colloidal solution can be conveyed by a low pressure pump for example a pump using a pressure of 7 bar or lower, i.e. about $7 \cdot 10^5$ Pascals.

The break-up of the gel onto the surface can be obtained using for example a flat jet nozzle or a round jet nozzle.

The distance between the pump and the nozzle may be any distance and for example may be between 1 and 50 m, in particular 1 to 25 m.

The sufficiently short viscosity recovering time of the gels used according to the invention allows the sprayed gel to adhere to any surfaces e.g. to walls.

The amount of gel deposited on the surface to be treated is generally 100 to 2000 g/m$^2$, preferably 500 to 1500 g/m$^2$, more preferably 600 to 1000 g/m$^2$.

The amount of gel deposited per unit surface area and hence the thickness of the deposited gel influences the drying rate.

For example, when a gel film, layer, having a thickness of 0.5 mm to 2 mm is sprayed onto the surface to be treated, the efficient contact time between the gel and the materials is then equivalent to its drying time, a period during which the active ingredient contained in the gel interacts with the biofilm.

In addition it has surprisingly been shown that the amount of deposited gel, when it lies within the above-mentioned ranges and in particular when it is higher than 500 g/m$^2$ and particularly within the range of 500 to 1500 g/m$^2$ which corresponds to a minimum thickness of deposited gel greater than 500 μm for example for a quantity of deposited gel higher than 500 g/m$^2$, allows fracturing of the gel to be obtained after drying in the form of millimeter-size flakes for example having a size of 1 to 10 mm, preferably 2 to 5 mm which can be suctioned.

The amount of deposited gel and hence the thickness of deposited gel, preferably higher than 500 g/m$^2$ i.e. 500 μm, is the fundamental parameter impacting the size of the dry residues formed after drying of the gel, and which therefore ensures that dry residues of millimeter size are formed and not powdery residues, such residues being easy to remove using a mechanical method and preferably by suction.

However, it is also to be noted that, by means of the surfactant in low concentration, the drying of the gel is improved and leads to a phenomenon of homogenous fracturing with dry residues of monodisperse size and increased capability of the dry residues to detach themselves from the substrate.

The gel is left on the surface to be treated for the time required for drying thereof. Throughout this drying step, which can be considered to be the active phase of the method of the invention, the solvent contained in the gel i.e. generally the water contained in the gel evaporates until a dry, solid residue is obtained.

The drying time is dependent upon the composition of the gel within the concentration ranges of its constituents given above, but also as already indicated upon the amount of gel deposited per unit surface area i.e. the thickness of the deposited gel.

The drying time is also dependent on climate conditions namely temperature, ventilation and relative humidity of the atmosphere in which the solid surface finds itself.

The method of the invention can be implemented under extremely wide-ranging climate conditions namely a temperature T of 1° C. to 50° C. and relative humidity RH of 20% to 80%.

The drying time of the gel of the invention is therefore generally from 1 hour to 24 hours at a temperature T of 1° C. to 50° C. and relative humidity RH of 20% to 80%.

It is to be noted that the formulation of the gel used in the invention, in particular if it contains surfactants such as «Pluronics®», generally ensures a drying time substantially equivalent to the contact time between the gel and the biofilm that is necessary, required to destroy, remove the biofilm polluting the material. In other words, the formulation of the gel ensures a drying time that is none other than the time needed to remove, destroy the biofilm and is compatible with biofilm destruction kinetics and in particular the destruction kinetics of the biological contamination contained in the biofilm (the biological organisms are killed).

After drying of the gel, the gel fractures homogeneously giving dry, solid residues of millimeter size e.g. a size of 1 to 10 mm, preferably 2 to 5 mm that are non-powdery and generally in the form of solid flakes. The dry, solid residues contain compounds resulting from destruction of the biofilm.

The dry residues such as flakes obtained after drying adhere weakly to the surface of the cleaned material. On this account the dry residues obtained after drying of the gel can be easily recovered by mere brushing and/or suction. However the dry residues can also be evacuated using a jet of gas e.g. a jet of compressed air.

Therefore no rinsing is necessary and the method of the invention does not generate any secondary effluent.

According to the invention therefore, first major savings in chemical reagents are obtained compared with a washing decontamination method using a solution. Secondly, since waste is obtained in the form of a dry residue that can be directly suctioned, a rinsing operation with water or liquid is avoided. This evidently results in a reduction in the amount of effluent produced but also in notable simplification in terms of treatment and discharge means. In particular according to the invention, the waste obtained on completion of the treatment is not entrained into rainwater evacuation networks in breach of regulations.

On account of the mostly mineral composition of the gel used in the invention and low amount of waste produced, the dry waste can be stored or directed towards an evacuation channel without prior treatment.

For example in the frequent case in which 1000 grams of gel are applied per $m^2$ of treated surface, the weight of the dry waste produced is less than 300 grams par $m^2$.

The invention will now be described with reference to the following examples given as non-limiting illustrations.

EXAMPLES

Example 1

In this example the «anti-biofilm» gel tested in following Examples 2 and 3 is described and prepared.

It is an oxidising, alkaline, basic, mineral gel comprising water, 1 M sodium hydroxide, sodium hypochlorite, alumina and a surfactant.

This gel does not comprise any super-absorbent polymer.

The aluminium oxide is Aeroxide® Alu C marketed by EVONIK INDUSTRIES having a specific surface area of 100 $m^2/g$ (BET), the surfactant is Pluronic® PE6200 marketed by BASF, the sodium hydroxide is 1 M sodium hydroxide marketed by SIGMA-ALDRICH and the sodium hypochlorite contains 10 to 15% active chlorine marketed by SIGMA-ALDRICH.

The gel used in the invention is prepared as follows: the sodium hypochlorite solution is diluted to 50% with demineralised water. This solution, the surfactant and sodium hydroxide are mixed using a mechanical agitator equipped with a three-blade impeller, at a speed of 200 rpm for 3 to 5 minutes. The alumina is then gradually added to the reaction mixture progressively increasing the speed of agitation as and when viscosity increases to reach a final speed of about 400 to 600 rpm without any spattering. The gel is then held under agitation for 5 minutes.

The composition of the tested gel is given in Table 2 below.

TABLE 2

Composition of the tested gel.

| Composition | Weight percentages (%) |
|---|---|
| 1M NaOH | 44.5 |
| Sodium hypochlorite (10-15% act. chl.) diluted 50% | 42.5 |
| Alumina | 12 |
| Pluronic ® PE6200 | 1 |

Example 2

In this example a test was conducted with the «anti-biofilm» gel prepared in Example 1 to remove a biofilm from a vertical outdoor surface.

The «anti-biofilm» gel prepared in Example 1 was applied using a brush to part of the surface of an outside wall coated with a traditional sprayed coat.

The test was conducted at a temperature lower than 10° C., under relative humidity in the order of 50%.

After 48-hour drying, the formed flakes were moved by gentle brushing.

FIG. 1 (A, B, C) shows the appearance of the wall surface at the different steps of the test in this example, namely:

- the initial state of the wall (A);
- the appearance of the wall surface after application of the gel using a brush on a part of the wall surface, this part of the wall surface is therefore coated with wet gel (B);
- the appearance of the surface after 48-hour drying and removal of the dry gel flakes by gentle brushing (C).

It can visually be ascertained that the biofilm has effectively been removed from the part of the wall surface, treated, cleaned in accordance with the invention using the gel prepared in Example 1.

This test shows the efficiency of the use according to the invention of the alkaline oxidising gel prepared in Example 1 to remove a biofilm on a vertical surface.

For better quantifying of the action of the gel, image analysis was performed using ImageJ software.

Figure 2:
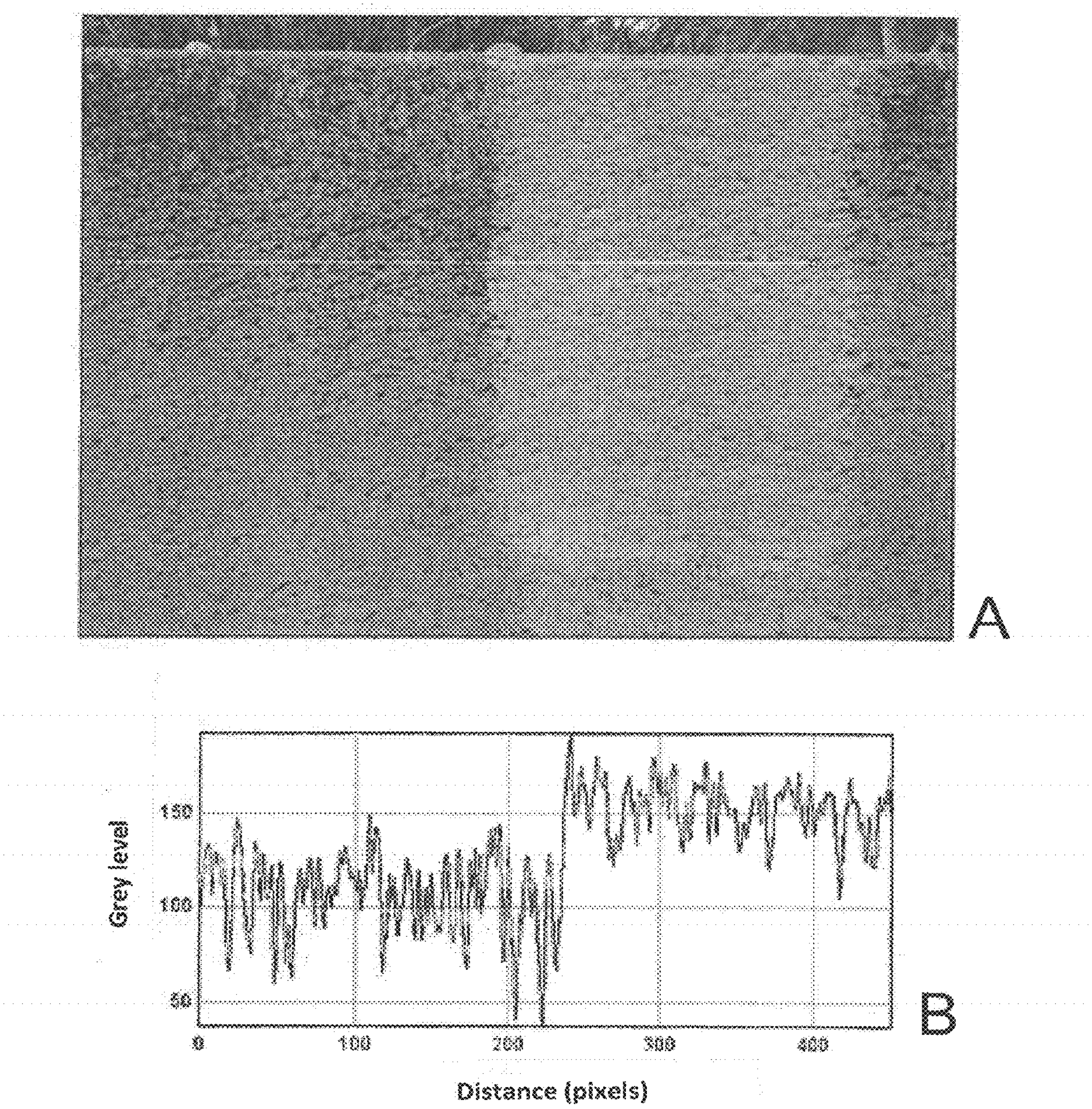
FIG. 2B is a graph showing the results of a grey values analysis carried out on the image in FIG. 1C converted to grey levels along the line drawn in FIG. 2A (similar to FIG. 1C).

To do so the final image in FIG. 1C showing the wall surface after treatment according to the invention was converted to grey levels (ranging from 0 black to 255 white) and analysis of the grey values was carried out along the line drawn in FIG. 2A (similar to FIG. 1C).

The mean value in the part of the wall surface non-treated with the gel of Example 1 is taken as reference.

The graph in FIG. 2B gives the results of image analysis and confirms the efficient removal of the biofilm by the gel in that part of the wall surface treated according to the invention with the gel prepared in Example 1.

Example 3

In this example, a test was conducted with the «anti-biofilm» gel prepared in Example 1 to remove a biofilm from a horizontal outdoor surface.

The «anti-biofilm» gel prepared in Example 1 was applied using a brush to a part of the surface of a balcony railing made of white cement.

The test was conducted at a temperature lower than 10° C., under relative humidity in the order of 50%.

After 48-hour drying the formed flakes were removed by gentle brushing.

Figure 3:
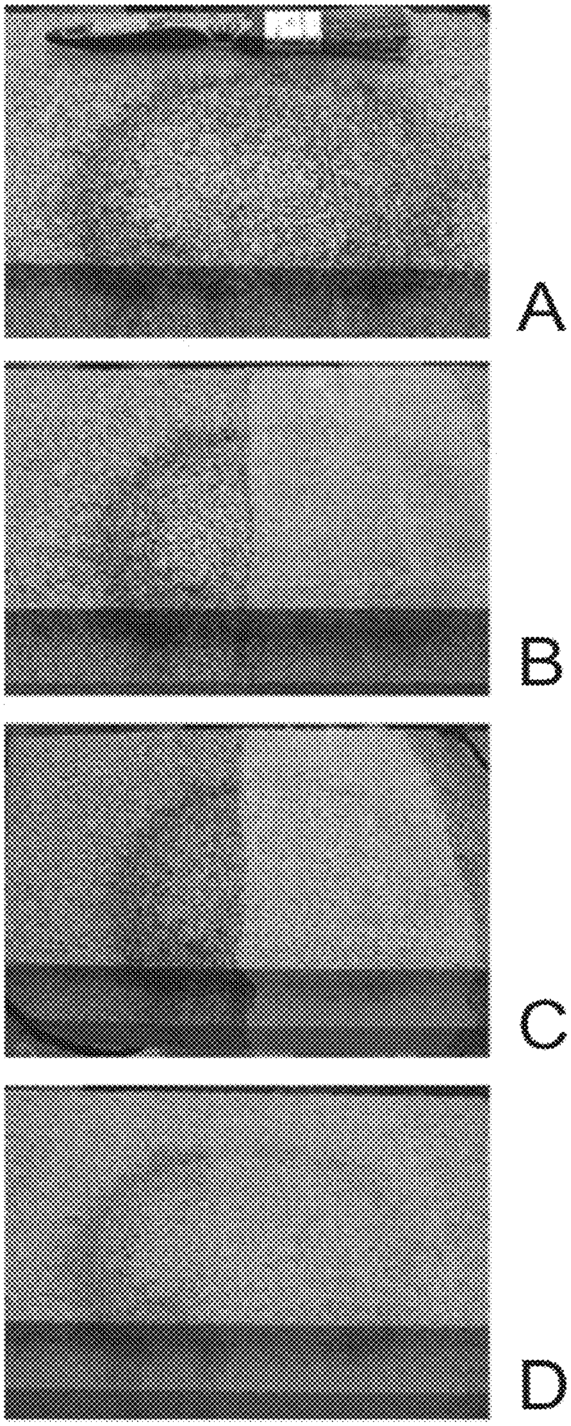
FIG. 3 (A, B, C, D) gives photographs showing the appearance of the surface of a rail treated according to the invention, at different steps of the test conducted in Example 3, namely: the initial state of the rail surface(A); the appearance of the rail surface after brush application of the gel to part of the surface of the rail (B); the appearance of the surface of the rail after 48-hour drying of the gel applied to part of the surface of the rail (C); the appearance of the surface of the rail after removal of the dry gel flakes by gentle brushing (D).

FIG. 3 (A, B, C, D) shows the appearance of the surface of the railing at the different steps of the test performed in this example, namely:

- the initial state of the part of the surface of the railing (A);
- the appearance of the surface of the railing after application of the gel using a brush onto part of the surface of the railing, this part of the railing surface is therefore coated with wet gel (B);
- the appearance of the surface after 48-drying of the gel applied to part of the railing surface, this part of the railing surface is therefore coated with dry gel (C);
- the appearance of the railing surface after removal of the dry gel flakes by gentle brushing (D).

It can visually be ascertained that the biofilm has effectively been removed from the treated part of the railing surface, cleaned according to the invention using the gel prepared in Example 1.

This test shows the efficiency of the use according to the invention of the alkaline oxidising gel prepared in Example 1 to remove a biofilm from a horizontal surface.

To better quantify the action of the gel, image analysis was carried out using ImageJ software as in Example 2.

To do so as in Example 2 the final image in FIG. 3D showing the rail surface after treatment according to the invention was converted to grey levels (ranging from 0 black to 255 white).

Figure 4:
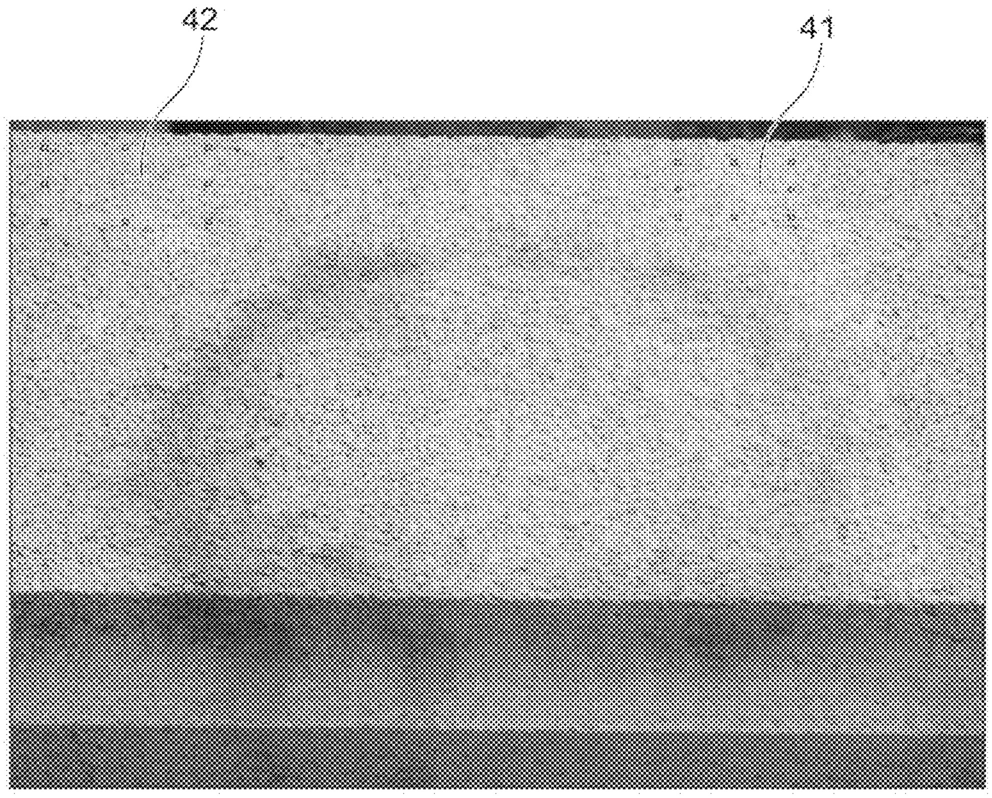
FIG. 4 shows the two areas of the surface of the rail (first area 41 located in the part of the surface treated with the gel and a second area 42 located in the part of the surface non-treated with the gel) for which an average greyscale was calculated in the image in FIG. 3D converted to grey levels.

On the other hand the difference being less distinct (strong background noise), the result is expressed in grey levels averaged over two areas of the railing surface, a first area 41 being located in that part of the surface treated with the gel and a second area 42 located in part of the surface non-treated with the gel (FIG. 4).

It is noted that the non-treated area has an average level of 156 whereas the treated area has an average grey level of 169.

The results of image analysis confirm the efficacy of biofilm removal by the gel in that part of the railing surface treated according to the invention using the gel prepared in Example 1.

REFERENCES

[1] NOBATEK Report http://www.nobatek.com/downloads/Etudes%20publiques/ENSEL%20Micro%20biologie%20_NOBATEK_.pdf

[2] US-A1-2012/0232153.

[3] «Biofilm quand les microbes s'o rganisent» by R. Briandet, L. Fechner, M. Naïali & C. Dreano, Editions Quae 2012.

[4] K. Ammerman, «*Algae, the growing problem*», Interface, January 2007, pages 37-42.

[5] FAURE S., FOURNEL B., FUENTES P., LALLOT Y. "*Procédé de traitement d'une surface par un gel de traitement, et gel de traitement*", FR-A1-2 827 530.

[6] FAURE S., FUENTES P., LALLOT Y. "*Gel aspirable pour la décontamination de surfaces et utilisation*", FR-A1-2 891 470.

[7] CUER F., FAURE S. «*Gel de décontamination biologique et procédé de décontamination de surfaces utilisant ce gel*», FR-A1-2962046 and WO-A1-2012/001046.

The invention claimed is:

1. A method, comprising removing a biofilm present on a surface of a solid substrate with a gel, wherein the gel is a colloidal solution comprising:

- 5% to 30% by weight, relative to the weight of the gel, of at least one inorganic viscosifying agent;
- a mineral base selected from the group consisting of hydroxides of alkaline metals, hydroxides of alkaline-earth metals and mixtures thereof, said mineral base being present in a proportion of 0.05 to 10 mol/L of gel;
- an oxidising agent stable in a basic medium selected from the group consisting of permanganates, persulfates, ozone, hypochlorites and the mixtures thereof, said oxidising agent stable in a basic medium being present in a proportion of 0.05 to 5 mol/L of gel;
- 0.1% to 2% by weight relative to the weight of the gel, of at least one surfactant;
- and a solvent;
- the gel not containing any super-absorbent polymer.

2. The method according to claim 1, wherein the mineral base is selected from among sodium hydroxide, potassium hydroxide and mixtures thereof, and the oxidising agent stable in the basic medium is selected from hypochlorites and mixtures thereof.

3. The method according to claim 2, wherein the gel comprises a combination of sodium hydroxide and sodium hypochlorite.

4. The method according to claim 1, wherein the inorganic viscosifying agent is selected from the group consisting of metal oxides, metalloid oxides with the exception of silica, metal hydroxides, metalloid hydroxides, metal oxyhydroxides, metalloid oxyhydroxides, aluminosilicates, clays, and the mixtures thereof.

5. The method according to claim 4, wherein the inorganic viscosifying agent consists of one or more aluminas.

6. The method according to claim 5, wherein the aluminas represent 5% to 30% by weight, relative to the total weight of the gel.

7. The method according to claim 1, wherein the surfactant is selected from among non-ionic surfactants; and the mixtures thereof.

8. The method according to claim 1, wherein the solvent is selected from the group consisting of water, organic solvents and the mixtures thereof.

9. The method according to claim 1, wherein the gel further comprises one or more mineral pigments.

10. The method according to claim 1, wherein the substrate comprises at least one material selected from the group consisting of metals and alloys; painted steels; organic polymers; glasses; cement materials; plasters; bricks; roof tiles; baked or unbaked earth; natural or artificial stones; coats; glass fibre; fibro-cements; asphalt; tar; slate; cellulose-based materials; and ceramics.

11. The method according to claim 1, wherein at least one cycle is performed comprising the following:

- a) applying the gel on said surface;
- b) maintaining the gel on the surface at least for a sufficient time so that the gel destroys the biofilm, and so that the gel dries and forms a dry, solid, non-powdery residue comprising compounds resulting from destruction of the biofilm; and
- c) removing the dry, solid, non-powdery residue comprising the compounds resulting from destruction of the biofilm.

12. The method according to claim 11, wherein the gel is applied to the surface of the solid substrate in the proportion of 100 g to 2000 g of gel per $m^2$ of surface area.

13. The method according to claim 11, wherein the gel is applied on the surface of the solid substrate by spraying, or using a brush or float.

14. The method according to claim 1, wherein the b) drying is conducted at a temperature of 1° C. to 50° C., under a relative humidity of 20% to 80%.

15. The method according to claim 11, wherein the gel is maintained on the surface for a time of 2 to 72 hours.

16. The method according to claim 11, wherein the dry, solid residue is in the form of particles having a size from 1 to 10 mm.

17. The method according to claim 11, wherein the dry, solid, non-powdery residue is removed from the surface of the solid substrate by brushing and/or suction.

18. The method according to claim 11, wherein the described cycle is repeated 1 to 10 times using the same gel for all cycles or using different gels for one or more cycles.

19. The method according to claim 11, wherein during the maintaining b), the gel, before complete drying, is re-wetted with a solution of mineral base and oxidising agent.

20. The method according to claim 7, wherein the non-ionic surfactants are selected from block copolymers, ethoxylated fatty acids; and the mixtures thereof.

21. The method according to claim 20, wherein said block copolymers are block copolymers of ethylene oxide and propylene oxide.

* * * * *